United States Patent [19]

Gogate et al.

[11] Patent Number: 5,703,111
[45] Date of Patent: Dec. 30, 1997

[54] STABLE INJECTABLE FORMULATION OF BMY-25067

[75] Inventors: Uday S. Gogate, North Brunswick; Shreeram N. Agharkar, Lawrenceville; Lawan Phusanti, Princeton, all of N.J.

[73] Assignee: Bristol-Myers Squibb Company, Princeton, N.J.

[21] Appl. No.: 760,237

[22] Filed: Dec. 4, 1996

Related U.S. Application Data

[60] Provisional application No. 60/010,004 Jan. 5, 1996.
[51] Int. Cl.$^6$ ................................................ A61K 31/40
[52] U.S. Cl. ................................... 514/410; 548/422
[58] Field of Search ........................ 548/422; 514/410

[56] References Cited

U.S. PATENT DOCUMENTS

| | | | |
|---|---|---|---|
| 4,691,023 | 9/1987 | Vyas et al. | 548/422 |
| 5,075,454 | 12/1991 | Benigni et al. | 548/422 |

*Primary Examiner*—Johann Richter
*Assistant Examiner*—Laura L. Stockton
*Attorney, Agent, or Firm*—William T. Han; Samuel J. DuBoff

[57] ABSTRACT

This invention relates to a stable, easy to constitute, injectable formulation of anticancer agent BMY-25067. More specifically, the present invention concerns a formulation of BMY-25067 obtained from lyophilizing a solution comprising up to 4 mg of BMY-25067 per mL of 65% t-butanol/water, further comprising about 2% PVP (K-12 or K-17), optionally comprising pharmaceutically acceptable carrier(s).

5 Claims, No Drawings

STABLE INJECTABLE FORMULATION OF BMY-25067

This application is related to provisional application Ser. No. 60/010,004 filed Jan. 5, 1996.

FIELD OF THE INVENTION

This invention concerns a stable, easy to constitute, injectable formulation of an anticancer agent.

BACKGROUND OF INVENTION

U.S. Pat. No. 4,691,023 issued Sep. 1, 1987 discloses the antitumor activity and synthesis of a mitocycin C analogue, BMY-25067 of the formula

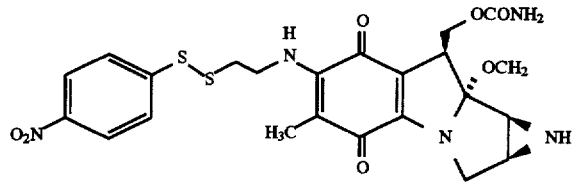

A totally aqueous formulation of BMY-25067 is impractical because of its extremely low water-solubility (0.3 μg/mL) at 25° C. Its solubility and/or stability in the presence of pharmaceutically acceptable cosolvents (e.g. ethanol, Cremophor®, dimethylacetamide, etc.) is also low, thus rendering a ready-to-use or a concentrate formulation unfeasible. When BMY-25067 is lyophilized with either no excipient or with commonly used excipients such as mannitol, sodium chloride, etc., the resultant lyophile does not readily reconstitute with aqueous diluents such as 5% Tween 80:phosphate buffer, but requires sonication for complete dissolution. Surprisingly, it has now been discovered that a formulation of BMY-25067 (50 mg/vial) containing 250 mg of polyvinyl pyrrolidone (K-12 or K-17), lyophilized from a 65% t-butyl alcohol:water mixture is stable (>90% potency remaining after 12 weeks storage at 50° C.). Also, this lyophile could be dissolved completely within 5–10 minutes when reconstituted with 5% Tween 80:phosphate buffer vehicle.

SUMMARY OF THE INVENTION

This invention relates to a stable, easy to constitute, injectable formulation of anticancer agent BMY-25067. More specifically, the present invention concerns a formulation of BMY-25067 obtained from lyophilizing a solution comprising up to 4 mg of BMY-25067 per mL of 65% t-butanol/water, further comprising about 2% PVP (K-12 or K-17), optionally comprising pharmaceutically acceptable carrier(s).

DETAILED DESCRIPTION

BMY-25067 is a semi-synthetic analogue of mitomycin C. It has murine antitumor activity superior to mitomycin C.

Solubility of BMY-25067 at 25° C. in water was determined in the following manner: a 10 mg aliquot was placed in a Type I flint glass vial, 2 mL of water was added to the vial, the suspension was stirred for four hours at ambient temperature (25° C.) while protected from light, and filtered through Gelman Acrodisc 0.2 micron filter. The filtrate was analyzed for BMY-25067 using the following HPLC method (hereinafter referred to as "the HPLC method"):

HPLC Method

Column—GL Sciences Intersil ODS-2; 4.6×150 mm, 5 μm,

Mobile phase A—37% acetonitrile in 0.015M ammonium acetate

Mobile phase B—80% acetonitrile in 0.015M ammonium acetate

Flow rate—2 mL/min.

Detection wavelength—369 nm

Gradient—100% mobile phase A for 11 minutes; then a 7 minute linear gradient to 100% mobile phase B and hold for 1 minute; linear gradient to 100% mobile phase A over 2 minutes; then re-equillibrate with mobile phase A for 9 minutes.

Using this method, the aqueous solubility of BMY-25067 was observed to be 0.3 microgram/mL. Until now, because of this low solubility, a totally aqueous formation of BMY-25067 has been impractical. In order to be able to deliver a daily dose of 100 mg BMY-25067 to a patient as a 30-minute bolus injection and for ease of handling, a minimum of 2 mg/mL dosing solution concentration is considered necessary.

Solubility of BMY-25067 at 25° C. in various parenterally suitable cosolvents and cosolvent:water mixtures was studied and the results are tabulated in Table 1. The procedure used for determination of solubility was similar to that for water described above. For the solvents providing adequate solubility (i.e. greater than 2 mg/mL), stability of the corresponding 2 mg/mL solutions was studied using the following procedure: BMY-25067 solution was initially analyzed for potency by the HPLC method as described above. Then an aliquot was placed in a Type I flint glass volumetric flask, and the light-protected flask was stored at the indicated temperature (Table 1) for the specified time. The solution was analyzed again for potency using the HPLC method. For the solvent systems studied in Table 1, none provided adequate solubility and stability, i.e., none of the >2 mg/mL solutions would retain 90% potency during storage for 12 months. These results suggested that a ready-to-use or a liquid concentrate formulation of BMY-25067 was not feasible.

Various lyophilized formulations of BMY-25067 were explored for stability and for ease of reconstitution. A cosolvent system of 5% Tween 80: 0.01M phosphate buffer (pH 7) was used as reconstitution vehicle because it provided the desired drug solubility (2 mg/mL) and adequate stability for the reconstituted solution (see Table 1). In one set of experiements, BMY-25067 solution (2 mg/mL) was prepared in 65% t-butanol:water mixture containing various excipients as shown in Table 2. A drug concentration of 4 mg/mL could be obtained only in the compositions containing polyvinyl pyrrolidone (i.e. PVP or Povidone). These solutions were filled in Type I amber glass vials and lyophilized using the following cycle: the solution was frozen at −40° C. for 5 hours, a vacuum (250 microns) was applied, primary drying was performed at shelf temperature of −20° C. for 36 hours, secondary drying was performed at 25° C. for 48 hours, vacuum was maintained at 100–250 micron by bleeding nitrogen gas throughout the drying process.

5% Tween 80: pH 7 phosphate buffer (0.01M) vehicle was added to vials of various lyophilized formulations (to achieve 2 mg/mL) and the reconstitution behaviors were observed. As the results in Table 2 suggest, only the compositions containing PVP could be reconstituted in 5–10 minutes without sonication. All the other compositions needed >10 minutes (including 2 minutes of sonication) for complete dissolution, and therefore were considered unacceptable.

Stability of the formulations containing PVP K-12 and PVP K-17 was studied after storage for 12 weeks at 50° C. Both of these formulations were observed to be chemically stable (91% and 95% potency remaining) as well as physically stable (i.e. appearance unchanged and reconstitution behavior unchanged).

Accordingly, the formulations containing BMY-25067 (50 mg/vial) and PVP (K-12 or K-17, 250 mg/vial), lyophilized from a solution in 65% t-butanol:water are easy to reconstitute using 5% Tween: pH 7 phosphate buffer vehicle, and are stable from physico-chemical viewpoint. The fact that most commonly used excipients (Table 2) did not provide the desired dissolution/stability profile—while addition of PVP rendered these formulation characteristics—was unique and surprising.

In summary, the present invention concerns a formulation of BMY-25067 obtained by lyophilizing a solution comprising up to 4 mg of BMY-25067 per mL of 65% t-butanol/water, further comprising about 2% PVP (K-12 or K-17), optionally comprising one or more pharmaceutically acceptable carriers. Preferably the lyophilized material is obtained from a solution containing 4 mg of BMY-25067 per mL of 65% t-butanol/water, further containing about 2% PVP (K-12 or K-17), optionally containing one or more pharmaceutically acceptable carriers.

As used herein, a pharmaceutically acceptable carrier is a material that is nontoxic and generally inert and does not affect the functionality of the active ingredients adversely. Examples of pharmaceutically acceptable carriers are well known and they are sometimes referred to as dilutents, vehicles or excipients. The carriers may be organic or inorganic in nature. Examples of pharmaceutically acceptable carriers that may be present in the present lyophilized formulations may be gelatin, lactose, starch, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. Preferred pharmaceutical carrier is mannitol in about 1.5%. In addition, the formulation may contain minor amounts of additives such as flavoring agents, coloring agents, thickening or gelling agents, emulsifiers, wetting agents, buffers, stabilizers, and preservatives such as anti-oxidants.

TABLE 1

Solubility of BMY-25067 in various cosolvents and cosolvent:water mixtures and stability of the formed solutions.

| Solvent system used | Solubility at 25° C. (mg/mL) | Stability of 2 mg/mL solutions |
|---|---|---|
| Ethanol | 5.4 | 66% remaining after 7 days at 25° C. |
| t-Butanol | 4.4 | 77% remaining after 5 days at 40° C. |
| t-Butanol:ethanol (90:10) | 3.4 | 68% remaining after 7 days at 25° C. |
| 5% dimethylacetamide:water | <0.01 | Not studied |
| 5% Polyethylene glycol 400:water | <0.01 | Not studied |
| 5% Pluronic F68 | <0.01 | Not studied |
| Cremophor | >2 | 87% remaining after 7 days at 25° C. |
| 5% Cremophor:water | >2 | 87% remaining after 1 day at 25° C. |
| 5% Brij 35:water | >2 | 93% remaining after 1 day at 25° C. |
| Tween 80 | >2 | 53% remaining after 4 days at 50° C. |

TABLE 1-continued

Solubility of BMY-25067 in various cosolvents and cosolvent:water mixtures and stability of the formed solutions.

| Solvent system used | Solubility at 25° C. (mg/mL) | Stability of 2 mg/mL solutions |
|---|---|---|
| Tween 80 + propyl gallate (0.5% w/v) | >2 | 79% remaining after 4 days at 50° C. |
| 80% Tween 80:pH 6.5 phosphate buffer + propyl gallate (0.5% w/v) | >2 | 66% remaining after 1 day at 50° C. |
| 5% Tween 80:pH 7 phosphate buffer (0.01M) | 5.8 | 95% remaining after 24 hours at 25° C. |

TABLE 2

Reconstitution behavior of various lyophilized formulations of BMY-25067.

| Excipient used[1] | Time needed for complete dissolution when using 5% Tween 80:phosphate buffer as diluent. |
|---|---|
| None | >10 minutes[2] |
| 1% Mannitol | >10 minutes[2] |
| 2% Maltose | >10 minutes[2] |
| 2% Dextrose | >10 minutes[2] |
| 2% Nicotinaminde | >10 minutes[2] |
| 2% Sodium chloride | >10 minutes[2] |
| 1% Sodium chloride | >10 minutes[2] |
| 2% Polyvinyl pyrrolidone (PVP, K-17) | 5–10 minutes |
| 2% PVP (K-12) | 5–10 minutes |
| 2% PVP (K-17), 1.5% mannitol | 5 minutes |

[1] Solutions containing excipient and BMY-25067 (2 mg/mL) in 65% t-butanol:water were filled in amber-glass vials and lyophilized. 4 mg/mL drug concentration was used for solutions containing PVP.
[2] Included ~2 minutes of sonication

What is claimed is:

1. A pharmaceutical formulation of BMY-25067 obtained from lyophilizing a solution comprising up to 4 mg of BMY-25067 per mL of 65% t-butanol/water, further comprising about 2% PVP (K-12 or K-17), optionally comprising one or more pharmaceutically acceptable carriers.

2. A pharmaceutical formulation of BMY-25067 as claimed in claim 1 obtained from a solution containing 4 mg of BMY-25067 per mL of 65% t-butanol/water, further containing about 2% PVP (K-12 or K-17), optionally containing one or more pharmaceutically acceptable carriers.

3. A pharmaceutical formulation as claimed in claim 1 or 2 which comprises 1.5% mannitol as a pharmaceutically acceptable carrier.

4. A method of obtaining a pharmaceutical formulation of BMY-25067 comprising the steps of: (a) freezing the solution comprising up to 4 mg of BMY-25067 per mL of 65% t-butanol/water, further comprising about 2% PVP (K-12 or K-17), and optionally comprising one or more pharmaceutically acceptable carriers, at −40° C. for 5 hours under a vacuum of 250 microns; (b) followed by primary drying at shelf temperature of −20° C. for 36 hours; (c) followed by secondary drying at 25° C. for 48 hours; while vacuum was maintained at 100–250 micron by bleeding nitrogen gas throughout the drying processes of steps (b) and (c).

5. A method of obtaining a pharmaceutical formulation of BMY-25067 as claimed in claim 4 comprising the steps of: (a) freezing the solution comprising 4 mg of BMY-25067 per mL of 65% t-butanol/water, further comprising about 2% PVP (K-12 or K-17), and 1.5% mannitol as a pharmaceutically acceptable carrier, at −40° C. for 5 hours under a vacuum of 250 microns; (b) followed by primary drying at shelf temperature of −20° C. for 36 hours; (c) followed by secondary drying at 25° C. for 48 hours; while vacuum was maintained at 100–250 micron by bleeding nitrogen gas throughout the drying processes of steps (b) and (c).

* * * * *